United States Patent [19]

Sutter

[11] Patent Number: 5,269,782
[45] Date of Patent: Dec. 14, 1993

[54] BIPOLAR MEDICAL COAGULATION AND CAUTERIZING INSTRUMENT

[75] Inventor: Hermann Sutter, Gundelfingen, Fed. Rep. of Germany

[73] Assignee: Select Medizin-Technik Hermann Sutter GmbH, Freiburg, Fed. Rep. of Germany

[21] Appl. No.: 869,662

[22] Filed: Apr. 16, 1992

[30] Foreign Application Priority Data

Apr. 22, 1991 [DE] Fed. Rep. of Germany ....... 4113037

[51] Int. Cl.$^5$ ............................................. A61B 17/39
[52] U.S. Cl. ..................................... 606/48; 606/50
[58] Field of Search ..................... 606/48, 50, 51, 52

[56] References Cited

U.S. PATENT DOCUMENTS 4,076,028  2/1978  Simmons ............................... 606/51
4,732,149  3/1988  Sutter ..................................... 606/50

FOREIGN PATENT DOCUMENTS 3409061  4/1985  Fed. Rep. of Germany.
3235570  6/1985  Fed. Rep. of Germany.

Primary Examiner—Lee S. Cohen
Attorney, Agent, or Firm—Darby & Darby

[57] ABSTRACT

A bipolar medical coagulation and/or cauterizing instrument has two elongated electrodes with first end portions which constitute the working end of the instrument and second end portions which are connectable to different poles of a high-frequency generator. The intermediate portions of the electrodes are surrounded by deformable insulators which are shrunk onto the respective electrodes and are confined in a tubular member serving to prevent the electrodes from moving relative to each other. To this end, the intermediate portions have cross sections which are out-of-round and/or which vary in the longitudinal direction of the respective electrodes. The insulators closely follow the outlines of the respective intermediate portions, and the tubular member closely follows the outlines of the insulators.

14 Claims, 1 Drawing Sheet

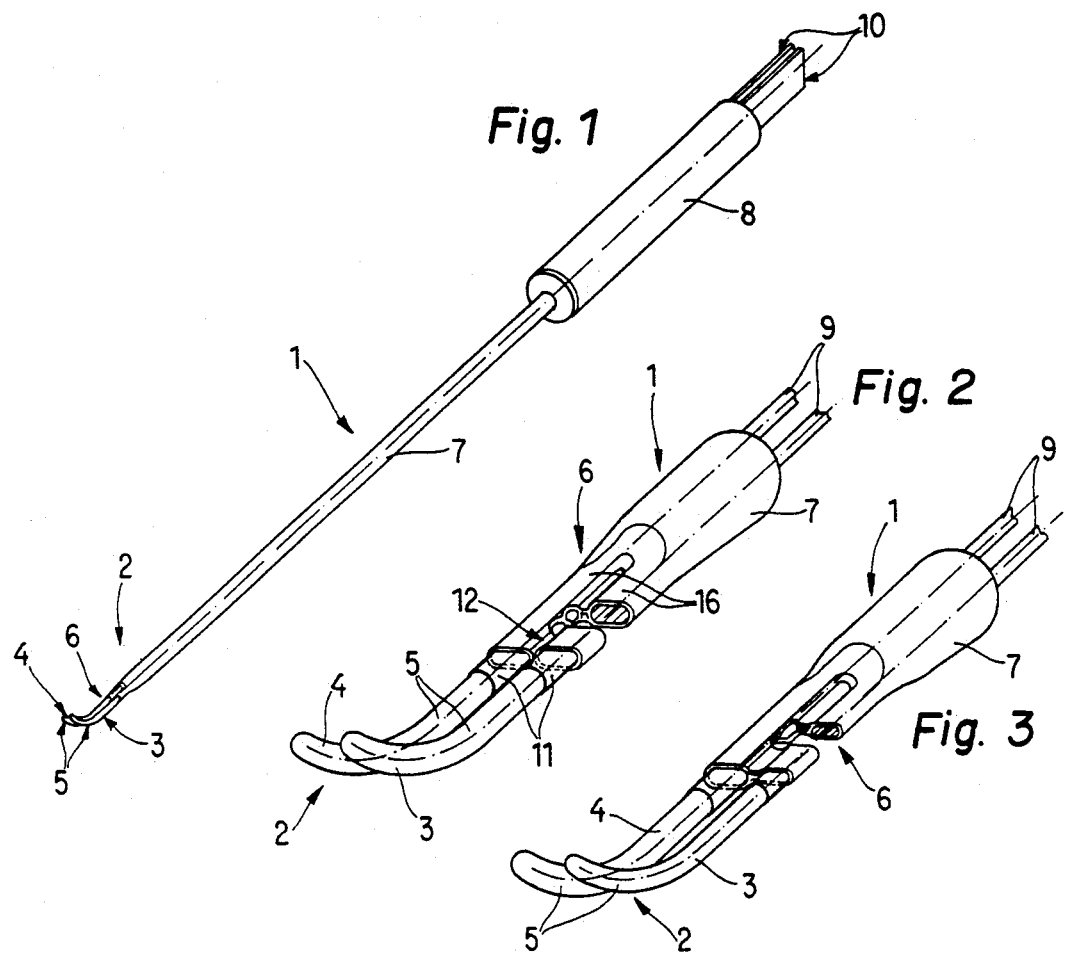
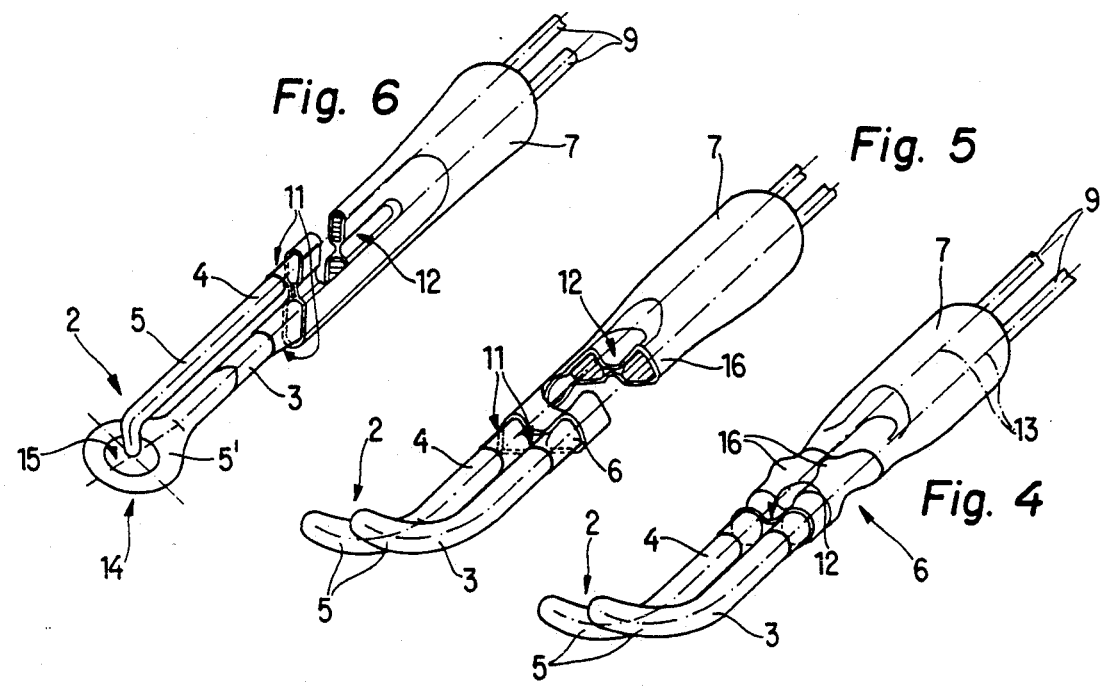

BIPOLAR MEDICAL COAGULATION AND CAUTERIZING INSTRUMENT

BACKGROUND OF THE INVENTION

The invention relates to bipolar medical instruments in general, and more particularly to improvements in bipolar medical instruments which can be utilized as coagulation instruments as well as for cutting of human and/or other animal tissue.

Bipolar medical coagulation instruments are well known in the art. Reference may be had, for example, to commonly owned U.S. Pat. No. 4,732,149 granted Mar. 22, 1988 for "Bipolar medical coagulation instrument" and to commonly owned German Pat. No. 34 09 061 granted Apr. 25, 1985. Such instruments can also be used for cauterizing if the exposed front end portions of their electrodes can convey currents which suffice to actually cut (by burning or searing) selected cells of tissue. It is then important that the front end portions of the electrodes be capable of standing large currents and that their mutual spacing remain constant, i.e., that such spacing cannot be changed in actual use of the instrument. The cutting action of such instruments is due to penetration of highly concentrated electrical oscillation energy into the tissue between the front end portions of the electrodes so that the tissue acts as a resistor and is heated with attendant destruction of selected cells.

Commonly owned German Pat. No. 32 45 570 (granted Jun. 27, 1985) discloses a bipolar coagulation instrument wherein the front end portions of the electrodes are inclined with respect to the adjacent intermediate portions of the respective electrodes in order to permit more convenient observation of the tissue which is to be treated. Such bending of the front end portions increases the likelihood of changes of orientation of the front end portions relative to each other; the changes of orientation entail a movement of the tips of the front end portions toward or away from each other with attendant pronounced changes in the coagulating or cutting action of the instrument. The patent proposes to avoid such changes of orientatuon by providing the intermediate portions of the electrodes with minute protuberances which extend into complementary recesses of a sleeve serving as a handle and surrounding the intermediate portions of the electrodes. The rear end portions of the electrodes extend beyond the handle and can be inserted into the socket of a plug at the end of a cable which, in turn, is connected to a high-frequency generator. Reference may be had to FIGS. 7 and 12 of German patent No. 32 45 570. Once used, the instrument of this German patent is or can be discarded; all that is necessary is to extract the terminals from the socket and replace the once used instrument with a new instrument. It has been found that the ability of the handle to hold the electrodes against angular and/or axial and/or other movements relative to each other is rather limited in spite of the provision of aforementioned minute protuberances and recesses. The same holds true for the manner of preventing rotation and/or other undesirable movements of electrodes relative to the handle of the instrument which is described and shown in the aforementioned commonly owned German Pat. No. 34 09 061.

OBJECTS OF THE INVENTION

An object of the invention is to provide a medical instrument which can be utilized for coagulation and/or cauterizing and wherein the electrodes are immobilized in their handle in a novel and improved way.

Another object of the invention is to provide novel and improved electrodes for use in the above outlined medical instrument.

A further object of the invention is to provide a novel and improved handle for the electrodes in the above outlined medical instrument.

An additional object of the invention is to provide the instrument with novel and improved means for electrically insulating the electrodes from each other and from the handle.

Still another object of the invention is to provide a novel and improved method of reducing the likelihood of movements of the electrodes relative to each other.

A further object of the invention is to provide a novel and improved method of reliably locking the electrodes to the handle of the above outlined medical instrument.

Another object of the invention is to provide a medical instrument which can be utilized as a coagulation instrument or as a cauterizing instrument and wherein the exposed portions of the electrodes at the working end of the instrument are capable of standing all kinds of stresses including those which tend to turn the electrodes about their respective axes, those which tend to move the one and/or the other electrode longitudinally of the handle as well as those which tend to pivot the front end portions of the electrodes relative to the handle and/or to bend such front end portions relative to the adjacent intermediate portions.

An additional object of the invention is to provide the electrodes of the above outlined medical instrument with novel and improved electrodes which are particularly suitable for cutting of tissue.

Still another object of the invention is to provide electrodes which can stand elevated temperatures when the instrument is used as a means for cutting human or other animal tissue.

A further object of the invention is to provide a reusable bipolar medical coagulation and/or cauterizing instrument.

SUMMARY OF THE INVENTION

The invention is embodied in a bipolar medical instrument which comprises two elongated electrodes having neighboring first end portions, second end portions and intermediate portions between the respective first and second end portions. The instrument further comprises means for insulating the electrodes from each other, and such insulating means comprises two tubular insulators each of which surrounds and closely follows the outline of the surrounded part of one of the intermediate portions. Still further, the instrument comprises means for preventing movements of the electrodes relative to each other, and such preventing means comprises a tubular member which confines the intermediate portions of the electrodes and has sections which closely follow the outlines of the insulators.

The intermediate portions of the electrodes and the insulators can have outlines which are out-of-round. For example, at least one of the intermediate portions and the respective insulator can have a polygonal outline. Furthermore, the intermediate portions of the electrodes and the insulators can have cross sections which are offset sideways relative to each other as seen in the longitudinal direction of the respective electrodes. For example, at least one of the intermediate portions and the respective insulator can have an undulate shape in the longitudinal direction of the respective electrode.

At least one of the insulators can include or constitute a deformable hose which is shrunk onto the respective intermediate portion.

The first end portion of at least one of the electrodes can be inclined relative to the respective intermediate portion; for example, such first end portion can be at least substantially normal to the respective intermediate portion. The intermediate portions of the electrodes can be substantially parallel to each other, the same as the two first end portions, and each first end portion can be inclined relative to the respective intermediate portion.

The first end portion of one of the electrodes can project beyond the tubular member through a first distance, and the first end portion of the other electrode projects beyond the tubular member through a second distance which can equal or approximate the first distance.

The first end portions of the electrodes can have different shapes and/or different cross sections. For example, the first end portion of one of the electrodes can have a first cross section and the other of the two first end portions can have a second cross section which is larger than the first cross section. At least one of these cross sections can be at least substantially circular.

The electrodes can be disposed in a common plane, and at least one of the two first end portions can be inclined toward the other first end portion in such common plane.

At least one of the electrodes can consist (at least in part) of a first material, and at least a portion of the other of the electrodes can consist (at least in part) of a different second material.

One of the first end portions can include or constitute an annulus (such as a ring) which surrounds an opening, and the tip of the other first end portion can extend at least close to or actually into the opening.

One of the electrodes can consist (at least in part) of a heat-resistant material (e.g., tungsten), and the other electrode can consist (at least in part) of a different second material, e.g., steel.

Another feature of the invention resides in the provision of a bipolar medical instrument which comprises two elongated electrodes having neighboring first end portions, second end portions and intermediate portions between the respective first and second end portions. One of the first end portions includes an annulus (e.g., a ring) which surrounds an opening, and the tip of the other first end portion can extend at least close to or actually into the opening. The instrument further comprises means for preventing movements of the electrodes relative to each other, and such preventing means surrounds the intermediate portions of the electrodes.

The novel features which are considered as characteristic of the invention are set forth in particular in the appended claims. The improved medical instrument itself, however, both as to its construction and the mode of making the same, together with additional features and advantages thereof, will be best understood upon perusal of the following detailed description of certain presently preferred specific embodiments with reference to the accompanying drawing.

BRIEF DESCRIPTION OF THE DRAWING

FIG. 1 is a perspective view of a bipolar medical coagulation and/or cauterizing instrument which embodies one form of the invention;

FIG. 2 is an enlarged view of a detail at the working end of the instrument of FIG. 1, with portions of the electrodes, insulators and tubular member broken away and/or shown in section;

FIG. 3 is a similar enlarged fragmentary perspective view of a modified instrument wherein the cross section of the first end portion of one of the electrodes is larger than the cross section of the first end portion of the other electrode;

FIG. 4 is a similar enlarged fragmentary perspective view of a third instrument wherein the intermediate portions of the electrodes and the respective insulators have an undulate shape as seen in the longitudinal direction of the respective electrodes;

FIG. 5 is a similar enlarged fragmentary perspective view of a fourth instrument wherein the intermediate portions of the electrodes and the insulators have a substantially triangular cross-sectional outline; and FIG. 6 is a similar enlarged fragmentary perspective view of a fifth instrument wherein the first end portion of one of the electrodes includes a ring and the tip of the first end portion of the other electrode extends centrally into the opening within the ring.

DESCRIPTION OF PREFERRED EMBODIMENTS

FIG. 1 shows a bipolar medical coagulation and/or cauterizing instrument 1 having a working end 2 and comprising two elongated electrodes 3, 4. These electrodes have first end portions 5 at the working end 2 and flat second end portions 10 which constitute electrical terminals and are connectable to different poles of an energy source such as a high-frequency generator of the type described and shown in the aforementioned commonly owned German Pat. No. 32 45 570. When the instrument 1 is in use, high-frequency electric current flows as vibration energy through the tissue of a patient's body between the end portions 5 of the electrodes 3 and 4. The electrical resistance of the tissue causes controlled destruction of cells with simultaneous generation of heat. The instrument 1 can be used for point coagulation or for cauterization (cutting) of the tissue.

The intermediate portions 6 of the electrodes 3 and 4 are confined in a tubular member 7 (hereinafter called sleeve for short) which serves as a means for preventing angular and/or longitudinal movements of the electrodes relative to each other. The rear portion of the sleeve 7 (namely the portion adjacent the end portions or terminals 10) is provided with or constitutes a handle 8 which is grasped by the hand of the surgeon when the instrument 1 is in use. In order to be introduced into a patient's body, the sleeve 7 is first introduced into a trocar (not shown) which is thereupon caused to penetrate a selected portion of the body in a manner not forming part of the present invention.

Elongated parts of intermediate portions 6 of the electrodes 3 and 4 constitute conductors (shown in FIG. 2, as at 9) each of which is electrically connected to or is of one piece with the respective terminal 10. These conductors extend through the handle 8 because the latter is located in front of the terminals 10. The terminals 10 can be inserted into a socket (not shown)

which, in turn, is connected with the high-frequency energy source by a suitable cable.

FIG. 2 shows that the intermediate portions 6 of the electrodes 3 and 4 have a cross-sectional outline which is out-of-round. These intermediate portions are surrounded by tubular insulators 11 each of which preferably constitutes a length of elastically deformable hose shrunk onto and therefore closely following the outline of the respective intermediate portion 6. The intermediate portions 6 which are shown in FIG. 2 have a substantially rectangular (i.e, a polygonal) cross-sectional outline, the same as the insulators 11. The corresponding sections 16 of the sleeve 7 closely follow the outlines of and confine the insulators 11 to thus prevent any turning of the electrodes 3, 4 relative to each other. That part of the sleeve 7 which is disposed between the sections 16 surrounding the insulators 11 is flattened at 12 to thus further ensure that the intermediate portions 6 of the electrodes 3, 4 cannot move nearer to each other, even if the first end portions 5 at the working end 2 are subjected to pronounced stresses while the instrument 1 is in use. The material of the sleeve 7 is preferably ductile so that it can be deformed in a manner as shown in FIG. 2, i.e., to ensure that the sections 16 closely follow the outlines of the insulators 11 (and hence the outlines of intermediate portions 6 of the electrodes 3, 4); this reliably prevents any shifting of the electrodes relative to each other. Such prevention of any movements of the electrodes 3, 4 relative to each other is even more reliable if the cross sections of the intermediate portions 6 vary in the longitudinal direction of the respective electrodes. This will be described in greater detail with reference to FIG. 4. In each of the illustrated embodiments, the sections 16 of the sleeve 7 preferably form-lockingly surround the insulators 11 and the insulators are shrunk onto the respective intermediate portions 6 to thus form-lockingly surround the corresponding electrodes 3, 4 when the assembly of the instrument 1 is completed.

The just described configuration of the intermediate portions 6 and of the surrounding sections 16 of the sleeve 7 ensures that the end portions 5 of the electrodes 3, 4 can be subjected to pronounced stresses in the longitudinal direction of the respective electrodes as well as to stresses which tend to turn the electrodes about the preferably parallel axes of the intermediate portions without causing any shifting of the electrodes relative to one another. As already mentioned above, the part 12 of the sleeve 7 between the insulators 11 also contributes to prevention of movements of the electrodes 3, 4 relative to each other, particularly to prevention of any movements of the intermediate sections 6 toward or away from one another.

The intermediate portions 6 can receive their substantially rectangular (out-of-round) shape as a result of flattening in a suitable tool or machine, and such flattening can precede the shrinking of electrical insulators 11 onto the respective intermediate portions. The electrical insulators 11 are hoses of requisite length to ensure that the electrodes 3, 4 are satisfactorily insulated from each other and from the sleeve 7. Once the application of the insulators 11 is completed, they are confined in the sleeve 7 and the latter is deformed so that its deformed sections 16 closely follow the outlines of the insulators and, accordingly, the outlines of flattened intermediate portions 6 of the electrodes 3 and 4. The cross sections of the flattened intermediate portions 6 can vary in the longitudinal direction of the electrodes 3, 4 to thus even further reduce the likelihood of longitudinal movements of the electrodes relative to each other when the assembly of the instrument 1 is completed.

The feature that the end portions 5 of the electrodes 3, 4 in the assembled instrument 1 cannot turn relative to each other is of considerable importance in connection with numerous applications of the assembled instrument 1, especially if the bent foremost parts of the end portions 5 are subjected to twisting or torsional stresses which tend to turn the end portions 5 relative to each other and/or relative to the respective intermediate portions 6. In other words, the improved instrument 1 is assembled in such a way that the sleeve 7 ensures reliable retention of the end portions 5 in selected positions relative to each other, not only as concerns the distance between such end portions but also as concerns their orientation relative to one another and relative to the respective intermediate portions 6.

FIGS. 1 to 5 show that the end portions 5 of both electrodes are inclined, at least in part (particularly their foremost parts) relative to the respective intermediate portions 6. The extent of inclination can vary and can amount to as much as 90 degrees (note the upper electrode 4 of FIG. 6). FIGS. 1 to 5 further show that at least the foremost parts of the end portions 5 are bent in the same direction and substantially to the same extent from the common plane of the major parts of the electrodes 3 and 4, i.e., from the common plane of the intermediate portions 6. Such inclination of parts of, or of the entire, end portions 5 is desirable and advantageous in connection with numerous utilizations of the instrument 1 because the surgeon in charge of manipulating the instrument can readily observe the tissue at the locus where the tissue is contacted by the bent parts of the end portions 5. Still further, FIGS. 1 to 5 show that the extent to which the end portion 5 of the electrode 3 projects beyond the front end of the sleeve 7 is or can be the same as the extent to which the front end portion 5 of the electrode 4 projects beyond the front portion of the sleeve. This contributes to convenience of manipulation of the instrument and simplifies the assembly of the electrodes 3, 4 with the insulators 11 and sleeve 7.

The tips of the end portions 5 of the electrodes 3 and 4 which are shown in FIGS. 1 to 5 are rounded, and the cross sections of the end portions 5 shown in FIGS. 1-2, 4 and 5 are identical or similar all the way from the rounded tips to the front portions of the respective sleeves 7. Such end portions 5 are particularly suited for point coagulation of tissue. It is further within the purview of the invention to provide the electrodes 3 and 4 with first or front end portions which resemble or constitute hooks, eyelets (note the lower electrode 3 of FIG. 6) or otherwise depart from the shapes shown in FIGS. 1 to 5; this depends on the intended use of the instrument 1, i.e., on that part of the anatomy which is to be subjected to a coagulation or cauterization treatment. It is often advisable to impart to the end portions 5 the shape of eyelets or another rounded shape, particularly if the working end 2 of the instrument is to pass through the flap valve or valves of a trocar which is used to introduce the end portions 5 or similar or analogous end portions into the body of a patient.

The insulators 11 are or can be relatively thin and readily deformable so that they can accurately follow the outlines of the intermediate portions 6 of the respective electrodes 3 and 4. Moreover, this enables the surrounding sections 16 of the sleeve 7 to closely follow the outlines of the shrunk insulators 11, i.e., actually the outlines of the intermediate portions 6. This, too, contributes to the ability of the deformed sections 16 of the sleeve 7 to prevent any movements of the electrodes 3 and 4 relative to each other, even if the end portions 5 are subjected to very pronounced stresses acting in the axial and/or circumferential direction of the respective electrodes and/or to stresses which tend to pivot or flex the end portions 5 relative to the respective intermediate portions 6. All that counts is to select insulators 11 which, after having been shrunk onto the respective intermediate portions 6, properly insulate the electrodes 3, 4 from each other while also permitting the surrounding sections 16 of the sleeve 7 to closely follow the outlines of the non-circular parts of the intermediate portions 6. The ability of the deformed sections 16 of the sleeve 7 to prevent turning of the electrodes 3, 4 about their respective axes is particularly important when the end portions 5 are bent (either entirely or in part) relative to the corresponding intermediate portions 6 because any, even slight, turning of the one or the other electrode about its longitudinal axis would result in a pronounced movement of the tips of the end portions 5 nearer to or further away from each other. Retention of a preselected distance between the tips of the end portions 5 is of particular importance when the instrument 1 is used to cut tissue because this involves the flow of large currents from one of the end portions 5, through the tissue and to the other end portion 5. Such large currents must be withstood by the tips of the end portions 5, and this is ensured if the preselected distance between such tips does not change in actual use of the instrument 1.

The shaping of the intermediate portions 6 so that they exhibit a cross section which is out-of-round presents no problems. Such shaping can be carried out in many types of existing and readily available tools and/or machines at a low cost and at a high frequency. Thus, all that is necessary is to flatten the originally circular rod-shaped intermediate portions 6 between a pair of jaws or claws in order to obtain the cross sections which can be seen in FIG. 2. On the other hand, such simple and inexpensive shaping or flattening suffices to greatly enhance the ability of the electrodes 3 and 4 to stand highly pronounced stresses which tend to change the orientation of their end portions 5 relative to each other.

It is clear that the insulators 11 need not necessarily be shrunk onto the intermediate portions 6 of the respective electrodes. However, such shrinking has been found to even further enhance the ability of the deformed sections 16 of the sleeve 7 (i.e., of tubular sections at both sides of the flattened central part 12) to closely follow the outlines of the intermediate portions 6. Moreover, a relatively thin hose of insulating material can be readily shrunk onto an intermediate portion 6 regardless of the exact outline of the intermediate portion, i.e., regardless of whether or not the intermediate portion has a triangular, square, rectangular, oval or other non-circular outline and regardless of whether the intermediate portion is straight, undulate or otherwise shaped in the longitudinal direction of the respective electrode.

FIG. 3 shows that the cross section of the end portion 5 of the electrode 4 is larger than the cross section of the end portion 5 of the electrode 3. The cross sections have a circular outline but the diameter of the left-hand end portion 5 is or can be much greater than (e.g., twice) the diameter of the right-hand end portion 5. The instrument 1 which embodies the structure of FIG. 3 is particularly suitable for use in connection with the cutting of tissue. The electrode 3 of FIG. 3 is the active electrode and the electrode 4 of FIG. 3 is the neutral electrode. The cutting action of the tip of the end portion 5 of the electrode 3 is particularly satisfactory if the instrument 1 of FIG. 3 is used as a means for cutting human or other animal tissue.

FIG. 4 shows that the intermediate portions 6 have an undulate shape as seen in the longitudinal direction of the respective electrodes 3 and 4. Otherwise stated, the cross sections of successive increments of the intermediate portions 6 are shifted sideways relative to each other as seen in the longitudinal direction of the electrodes 3 and 4. Such design even further reduces the likelihood of any longitudinal shifting of the electrodes 3, 4 relative to each other when the intermediate portions 6 are confined in the shrunk insulators and the insulators are confined in the adjacent sections 16 of the sleeve 7 whereby the sections 16 closely follow the outlines of the respective insulators. The phantom lines 13 denote the central longitudinal axes of the major parts of the two electrodes, and the cross sections of the intermediate portions 6 are dimensioned and configurated in such a way that parts of these intermediate portions project radially of the corresponding axes 13 to a different extent (as considered in the direction of the axes). The electrodes 3, 4 can be held against rotation about the respective axes 13 as a result of strong frictional engagement of the sleeve 7 with the insulators and/or as a result of partial flattening (if necessary) of the intermediate portions 6 and corresponding flattening of the surrounding sections 16 of the sleeve 7. At least in many instances, the feature that the intermediate portions 6 of the electrodes 3, 4 have an undulate shape (FIG. 4) alone suffices to prevent angular and/or longitudinal movements of the electrodes relative to each other. It has been found that a combination of features which are shown in FIG. 4 (undulate shape) and in FIGS. 1-3 and 5-6 (polygonal cross section) invariably ensures that the orientation of the first end portions 5 and/or 5' of the electrodes relative to each other remains unchanged and that the electrodes do not move longitudinally relative to each other during all kinds of uses for which the assembled instrument 1 is intended.

An advantage of the embodiment which is shown in FIG. 4 is that the sleeve 7 is in form-locking engagement with the insulators 11 (and hence with the intermediate portions 6 of the electrodes 3, 4) in the circumferential as well as in the axial directions of the electrodes. The other embodiments establish a form-locking connection between the sleeve 7 and the respective electrodes in the circumferential direction of the electrodes and at least a force-locking connection in the axial or longitudinal direction of the electrodes.

FIG. 5 shows that the intermediate portions 6 of the electrodes 3, 4 have a triangular cross-sectional outline. Such polygonal outline also ensures that the electrodes 3, 4 cannot turn relative to each other in actual use of the instrument. The configuration of those sections (16) of the sleeve 7 in the instrument of FIG. 5 which confine the insulators 11 closely conforms to the outlines of the triangular intermediate portions 6. It is clear that one of the intermediate portions 6 can have a first (e.g., triangular or square) outline in contrast to the other intermediate portion 6 which can have another (e.g., rectangular, pentagonal, hexagonal or oval) outline, as long as the outline is out-of-round.

Reliable retention of electrodes 3 and 4 in selected angular and axial positions relative to each other is important in connection with the use of the improved instrument 1 as a coagulation implement but is perhaps even more important when the instrument is used as a means for cauterizing (cutting) human or other animal tissue. A prerequisite for optimal cutting is the retention of a selected optimum distance between the exposed first end portions 5 and/or 5' of the electrodes. FIG. 6 shows a portion of an instrument which is particularly suited for use as a cutting implement. The foremost part 14 of the end portion 5' of the electrode 3 constitutes or resembles an annulus (e.g., a ring) which surrounds an opening or passage 15. The foremost part of the front end portion 5 of the electrode 4 is inclined relative to the respective intermediate portion at an angle of approximately or exactly 90° and its rounded tip extends at least close to or actually into the central portion of the opening 15.

The end portion 5' of FIG. 6 constitutes the neutral pole and the end portion 5 of FIG. 6 constitutes the active pole of the instrument. The arrangement may be such that the rounded tip of the end portion 5 of FIG. 6 extends at least close to or actually into the central plane of the front part 14, i.e., close to or into a plane halving the front part 14 into two flatter annuli which are mirror images of each other.

Since the active electrode (4 in FIG. 6) is normally heated to an elevated temperature in actual use of the instrument as a means for cutting animal tissue, the electrode 4 of FIG. 6 is preferably made (at least in part) of a material (e.g., tungsten) which can stand elevated temperatures even more than the other electrode. The electrode 3 of FIG. 6 can be made of a material (e.g., steel) other than the strongly heat-resistant material of the electrode 4.

Instruments wherein the end portions 5 and/or 5' have different cross sections (see FIGS. 3 and 6) can be used with particular advantage for the cutting of tissue. The electrode having an end portion 5 or 5' with a larger cross section is the neutral electrode (this applies for the electrodes 4 in FIGS. 3 and 6), the other electrode (3 in each of FIGS. 3 and 6) being the active electrode. The front end portion 5 or 5' of the neutral electrode can have a shape as shown in FIG. 3 or 6 as well as any one of a number of other shapes, e.g., such electrode can have a forked (e.g., bifurcated) or U-shaped configuration. The exact configuration of the front end portion of the neutral electrode will depend on the anatomy of that portion of a human or other animal body which is to be cauterized by the improved instrument.

It has been found that, when the electrodes 3, 4 are assembled with the insulators 11 and with the sleeve 7 in a manner as described hereinbefore, the orientation of their front end portions 5 and/or 5' relative to each other and/or relative to the sleeve 7 remains unchanged even if the front end portions are acted upon by forces which tend to tilt them relative to the sleeve 7 and/or by any other forces which would be likely to shift, turn and/or pivot the front end portions of electrodes in heretofore known bipolar coagulation or analogous instruments.

End portions 5 and 5' of the type shown in FIG. 6 can be utilized with considerable advantage in coagulation or cauterizing instruments of the aforedescribed type (i.e., wherein the sleeve 7 closely follows the outlines of non-circular portions of the electrodes) as well as in instruments wherein the electrodes are installed in a sleeve in a conventional manner, e.g., in a manner as disclosed in the aforementioned commonly owned German Pat. No. 32 45 570.

The active electrode 4 of the instrument which is shown in FIG. 6 can but need not be made of tungsten, as long as it can stand the temperatures which develop when the instrument is used to cut tissue. It has been determined that an active electrode which consists (or whose front end portion consists) of tungsten is capable of standing such temperatures.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A bipolar medical instrument comprising two elongated electrodes having neighboring first end portions, second end portions and intermediate portions between the respective first and second end portions; means for insulating said electrodes from each other, including tubular insulators surrounding and closely following outlines of said intermediate portions; and means for preventing movements of said electrodes relative to each other, including a tubular member confining said intermediate portions and having cross-sections closely following outlines of said insulators, said intermediate portions and said insulators having outlines which are out of round.

2. The instrument of claim 1, wherein at least one of said intermediate portions and the respective insulator has a polygonal outline.

3. The instrument of claim 1, wherein at least one of said insulators is a deformable hose which is shrunk onto the respective intermediate portion.

4. The instrument of claim 1, wherein the first end portion of at least one of said electrodes is inclined relative to the respective intermediate portion.

5. The instrument of claim 1, wherein said intermediate portions are substantially parallel to each other and said first end portions are substantially parallel to each other and are inclined relative to the respective intermediate portions.

6. The instrument of claim 1, wherein one of said first end portions extends beyond said tubular member through a first distance and the other of said first end portions extends beyond said tubular member through a second distance which equals or approximates said first distance.

7. The instrument of claim 1, wherein said first end portions have different shapes.

8. The instrument of claim 1, wherein said first end portions have different cross sections.

9. The instrument of claim 1, wherein one of said first end portions has a first cross section and the other of said first end portions has a second cross section larger than said first cross section.

10. The instrument of claim 9, wherein at least one of said cross sections is circular.

11. The instrument of claim 1, wherein at least a portion of one of said electrodes comprises a first material and at least a portion of the other of said electrodes comprises a different second material.

12. The instrument of claim 1, wherein one of said electrodes comprises a heat-resistant material.

13. The instrument of claim 12, wherein said one electrode contains tungsten.

14. The instrument of claim 1, wherein at least one of said electrodes contains steel.

* * * * *